United States Patent
Ohishi et al.

(10) Patent No.: US 8,480,614 B2
(45) Date of Patent: Jul. 9, 2013

(54) CONTRAST MEDIUM INJECTION MANAGEMENT APPARATUS, IMAGE DIAGNOSTIC APPARATUS, AND CONTRAST MEDIUM INJECTION APPARATUS

(75) Inventors: Satoru Ohishi, Otawara (JP); Takuya Sakaguchi, Shioya-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1689 days.

(21) Appl. No.: 11/391,259

(22) Filed: Mar. 29, 2006

(65) Prior Publication Data
US 2006/0224104 A1    Oct. 5, 2006

(30) Foreign Application Priority Data
Mar. 30, 2005 (JP) .................................. 2005-098204
Mar. 10, 2006 (JP) .................................. 2006-065755

(51) Int. Cl.
*A61M 1/00*    (2006.01)

(52) U.S. Cl.
USPC .................. 604/27; 604/151; 604/46; 604/47

(58) Field of Classification Search
USPC ...................................... 604/46, 47, 151, 27
See application file for complete search history.

(56) References Cited

U.S. PATENT DOCUMENTS

| 5,562,621 | A | * | 10/1996 | Claude et al. | ............ 604/100.03 |
| 5,807,321 | A | * | 9/1998 | Stoker et al. | .................... 604/65 |
| 6,339,718 | B1 | | 1/2002 | Zatezalo et al. | |
| 6,385,483 | B1 | * | 5/2002 | Uber et al. | .................... 600/431 |
| 6,643,537 | B1 | | 11/2003 | Zatezalo et al. | |

FOREIGN PATENT DOCUMENTS

| CN | 1909834 A | 2/2007 |
| JP | 2001-161825 | 6/2001 |
| JP | 2001-337998 | 12/2001 |
| JP | 2003-102724 | 4/2003 |

OTHER PUBLICATIONS

Office Action issued Mar. 29, 2011, in Japanese Patent Application No. 2006-065755 (with English translation).

* cited by examiner

*Primary Examiner* — Laura Bouchelle
(74) *Attorney, Agent, or Firm* — Oblon, Spivak, McClelland, Maier & Neustadt, L.L.P.

(57) ABSTRACT

A contrast medium injection management apparatus includes a measuring unit which repeatedly measures the injection amount of contrast medium injected from at least one contrast medium injection device into a subject to be examined, a cumulative injection amount calculating unit which repeatedly calculates a cumulative injection amount at the start of examination or after an arbitrary point of time from the injection amount, and a display unit which displays the cumulative injection amount.

19 Claims, 4 Drawing Sheets

CONTRAST MEDIUM INJECTION MANAGEMENT APPARATUS, IMAGE DIAGNOSTIC APPARATUS, AND CONTRAST MEDIUM INJECTION APPARATUS

CROSS-REFERENCE TO RELATED APPLICATIONS

This application is based upon and claims the benefit of priority from prior Japanese Patent Applications No. 2005-098204, filed Mar. 30, 2005; and No. 2006-065755, filed Mar. 10, 2006, the entire contents of both of which are incorporated herein by reference.

BACKGROUND OF THE INVENTION

1. Field of the Invention

The present invention relates to a contrast medium injection management apparatus which manages the injection amount of contrast medium and an image diagnostic apparatus and contrast medium injection apparatus each equipped therewith.

2. Description of the Related Art

In angiographic examination and medical treatment (interventional radiology) using a radiodiagnostic apparatus, a large amount of contrast medium must be used in some cases. The injection amount of contrast medium is approximately estimated from the bottle content of contrast medium used in the examination and the amount of contrast medium injected by an automatic contrast medium injector (see Jpn. Pat. Appln. KOKAI Publication No. 2003-102724).

BRIEF SUMMARY OF THE INVENTION

It is an object of the present invention to improve the management accuracy of the injection amount of contrast medium.

According to a first aspect of the present invention, there is provided a contrast medium injection management apparatus comprising a measuring unit which repeatedly measures the injection amount of contrast medium injected from at least one contrast medium injection device into a subject to be examined, a cumulative injection amount calculating unit which repeatedly calculates a cumulative injection amount at the start of examination or after an arbitrary point of time from the injection amount, and a display unit which displays the cumulative injection amount.

According to a second aspect of the present invention, there is provided a contrast medium injection management apparatus comprising a measuring unit which repeatedly measures the injection amount of contrast medium injected from at least one contrast medium injection device into a subject to be examined, a cumulative injection amount calculating unit which repeatedly calculates a cumulative injection amount at the start of examination or after an arbitrary point of time from the injection amount, and a display unit which displays a warning message when the cumulative injection amount exceeds a reference injection amount.

According to a third aspect of the present invention, there is provided a contrast medium injection management apparatus comprising a measuring unit which repeatedly measures the injection amount of contrast medium injected from at least one contrast medium injection device into a subject to be examined, a cumulative injection amount calculating unit which repeatedly calculates a cumulative injection amount at the start of examination or after an arbitrary point of time from the injection amount, and a display unit which displays an early alert message when the cumulative injection amount exceeds a predetermined ratio to a reference injection amount.

According to a fourth aspect of the present invention, there is provided a contrast medium injection management apparatus comprising a measuring unit which repeatedly measures the injection amount of contrast medium injected from at least one contrast medium injection device into a subject to be examined, a cumulative injection amount calculating unit which repeatedly calculates a cumulative injection amount at the start of examination or after an arbitrary point of time from the injection amount, and a display unit which displays an early alert message when the cumulative injection amount exceeds a predetermined ratio to a reference injection amount, and displays a warning message when the cumulative injection amount exceeds the reference injection amount.

According to a fifth aspect of the present invention, there is provided an image diagnostic apparatus comprising means for storing an examination routine having a plurality of imaging operations in sequence, means for storing a planned injection amount of contrast medium used for each imaging operation in the examination routine, means for calculating a total injection amount of contrast medium used in the examination routine from a planned injection amount of contrast medium used for each of the plurality of imaging operations, means for displaying a planned injection amount of contrast medium to be used for each of the plurality of injecting operations and the calculated total injection amount of contrast medium, and means for modifying the contrast medium amount for each examination in accordance with an instruction from an operator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
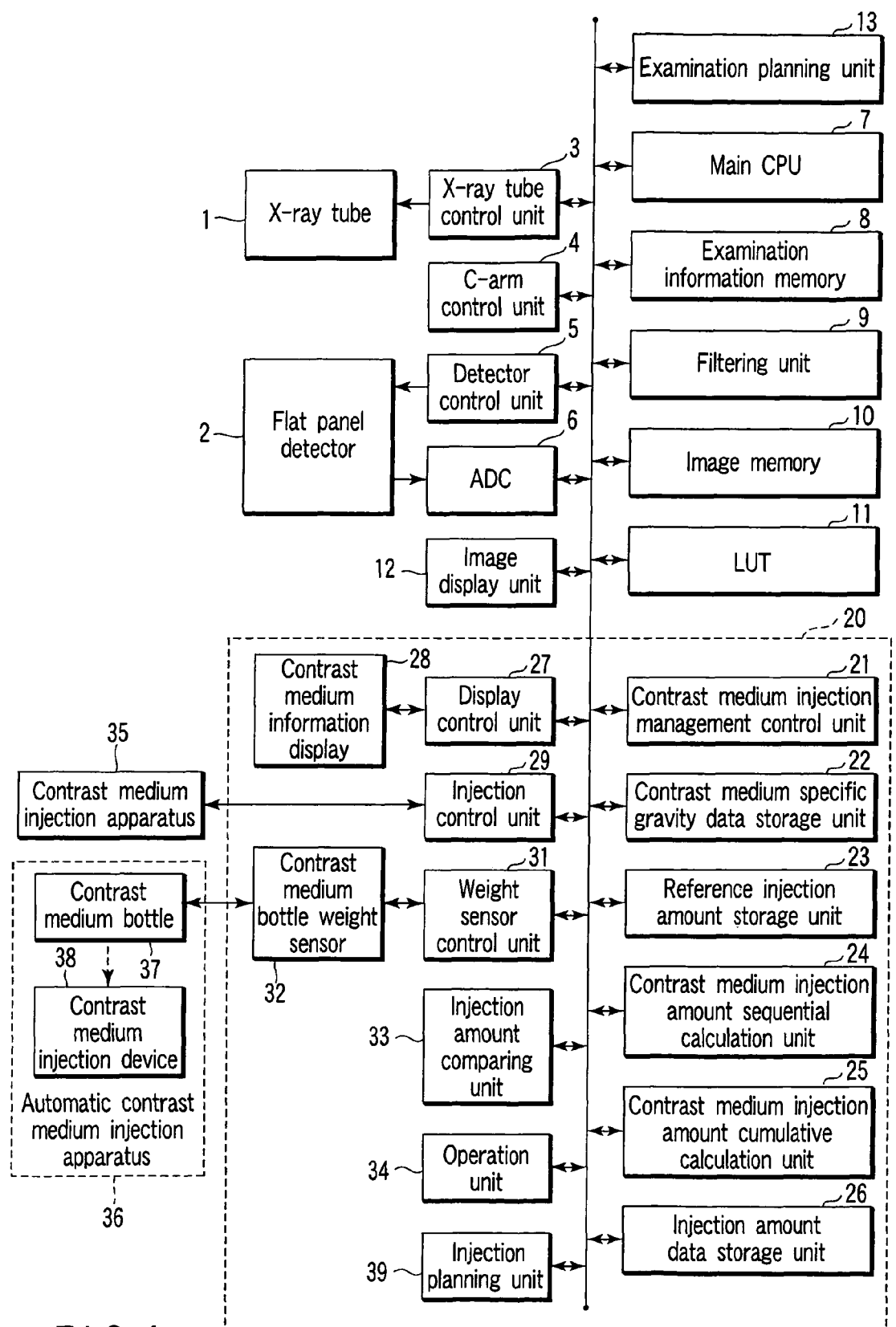
FIG. 1 is a block diagram showing the arrangement of an X-ray imaging apparatus according to an embodiment of the present invention.

FIG. 1 shows the arrangement of an image diagnostic apparatus according to an embodiment of the present invention. In this embodiment, an image diagnostic apparatus is typified by an X-ray imaging apparatus. However, the present invention is not limited to an X-ray imaging apparatus and can be applied to other modalities such as an X-ray digestive organ diagnostic apparatus, X-ray computerized tomographic apparatus (X-ray CT), magnetic resonance imaging apparatus (MRI), and ultrasound diagnostic apparatus as long as it is an image diagnostic apparatus using a contrast medium. In this case, an X-ray imaging apparatus will be exemplified.

The X-ray imaging apparatus is equipped with a contrast medium injection management apparatus 20. Note that the contrast medium injection management apparatus 20 may be provided as a stand-alone apparatus independently of the X-ray imaging apparatus. Contrast medium injection apparatuses 35 and 36 of a plurality of system are connected to the contrast medium injection management apparatus 20, and operate under the control of the contrast medium injection management apparatus 20. For the sake of descriptive convenience, the contrast medium injection apparatuses 35 and 36 are described separately from the contrast medium injection management apparatus 20. However, each of the contrast medium injection apparatuses 35 and 36 may be equipped with the contrast medium injection management apparatus 20.

A main CPU 7 of the X-ray imaging apparatus functions as the control center of the overall apparatus. An examination information memory 8 stores examination information ordered from an ordering system (not shown). Examination information includes an examination date, examination purpose, examination region, a designated type of contrast medium, and the like in addition to a patient code, name, height, weight, sex, and age.

An examination planning unit 13 plans an examination routine including a plurality of imaging steps in sequence on the basis of an examination purpose, examination region, and the like. For example, coronary artery examination is performed by an X-ray diagnostic apparatus in accordance with a predetermined routine. In general, the left coronary artery is imaged in six directions, and the right coronary artery is imaged in three directions. The left ventricle is then imaged in one direction to complete the imaging operation. Observing the images sensed in different directions makes it possible to check a bifurcation of interest. The data of a planned examination routine is stored in the examination information memory 8. The examination routine data includes the injection amount of contrast medium used in each imaging operation.

An X-ray tube 1 is typically mounted on a C-arm (not shown), together with a flat panel detector (FPD) 2 having a plurality of detection elements arranged two-dimensionally. The C-arm is supported on a base (not shown) so as to be arbitrarily movable and rotatable. A C-arm control unit 4 controls the movement and rotation of the C-arm. An X-ray tube control unit 3 has a high voltage generator. The X-ray tube control unit 3 applies a high voltage (tube voltage) between the cathode and anode of the X-ray tube 1 to generate X-rays from the X-ray tube 1, and also supplies a current to the filament. The flat panel detector 2 typically repeats cyclic operation of accumulating charge, reading out the charge, resetting, and the like under the control of a detector control unit 5. The signal typically read out as a voltage change from the flat panel detector 2 is converted into a digital signal by an analog/digital converter (ADC) 6, and is stored as image data in an image memory 10. The X-ray imaging apparatus is equipped with processing units for processing image data, e.g., a subtraction unit (not shown) which subtracts images obtained before and after the injection of a contrast medium at the same angle from each other, a filtering unit 9 which performs high-frequency enhancement filter and the like, an affine transformation unit (not shown) which performs image enlargement/movement and the like, and a look up table 11 which performs gray scale transformation. The processed image data is displayed on an image display unit 12 having a high-resolution display.

As described above, a plurality of contrast medium injection apparatuses (35 and 36 in this case) can be connected to the contrast medium injection management apparatus 20. One contrast medium injection apparatus 35 is of a type that has a function of measuring the injection pressure and injection amount of contrast medium and a setting function of setting an injection pressure and an injection amount from an injection control unit 29 with high accuracy. Note that in the following description, an "injection amount" is defined as the volume of contrast medium injected (the unit: cc). The other contrast medium injection apparatus 36 is a type that does not have the above measuring function or setting function, and typically has a contrast medium bottle 37 containing a contrast medium, an injection device 38 such as an injector connected thereto, and a base (not shown) from which the contrast medium bottle 37 is suspended. Even with the contrast medium injection apparatus 36 of this type, in order to measure an injection amount, the contrast medium injection management apparatus 20 comprises a weight sensor 32 having, for example, a piezoelectric element for detecting the weight of the contrast medium bottle 37. A weight sensor control unit 31 repeatedly measures the weight of the contrast medium bottle 37 in predetermined cycles during examination through the weight sensor 32, and calculates a change in weight from the previous measurement time.

According to the above description, the injection amount of contrast medium is detected by the measuring function of the contrast medium injection apparatus (injector) 35 and the weight sensor 32 of the contrast medium bottle 37. However, the present invention is not limited to this. For example, a flowmeter may be provided in a catheter or in a tube located immediately before the catheter, and the flow rate on the flowmeter may be monitored, thereby measuring it as the injection amount of contrast medium.

In addition to the injection control unit 29, weight sensor control unit 31, and weight sensor 32, the contrast medium injection management apparatus 20 has a contrast medium injection management control unit 21 for controlling the overall apparatus 20, a contrast medium specific gravity data storage unit 22 which stores specific gravity data unique to each type of contrast medium in advance, and a reference injection amount storage unit 23 for generating a reference injection amount corresponding to the physique of a subject. A reference injection amount is the upper limit of the injection amount of contrast medium per examination which is permitted to be injected into a subject to be examined including a certain margin for the purpose of safety, i.e., the recommended upper limit of the contrast medium injected into the subject during one examination period. In many cases, a specific organization or a contrast medium providing company sets a reference injection amount. A reference injection amount is set at a rate of 5 cc per kg in accordance with the weight as a physique of a subject. In the reference injection amount storage unit 23, a plurality of reference injection amounts are stored in association with a plurality of physiques (weights).

The contrast medium injection management apparatus 20 also has a contrast medium injection amount sequential calculation unit 24, contrast medium injection amount cumulative calculation unit 25, injection amount comparing unit 33, operation unit 34, display control unit 27, contrast medium information display 28, and injection amount data storage unit 26. The contrast medium injection amount sequential calculation unit 24 calculates the injection amount (the injection volume) of contrast medium from the contrast medium injection apparatus 36 from a change in the weight of the contrast medium bottle 37, which is periodically calculated by the weight sensor control unit 31, and a specific gravity unique to the used contrast medium, and also adds the injection amount of contrast medium from the contrast medium injection apparatus 35, which is acquired from the injection control unit 29, to the calculated injection amount, thereby repeatedly calculating an increase in the total injection amount of contrast medium from one or a plurality of contrast medium injection apparatuses (35, 36) into the subject. The contrast medium injection amount cumulative calculation unit 25 repeatedly calculates a cumulative injection amount as the total amount of contrast medium injected into the subject in the interval between the examination start time and the current time by accumulating increases in injection amount calculated by the injection amount sequential calculation unit 24 from the examination start time.

The injection amount comparing unit 33 calculates a possible injection amount, which represents the actual remaining injection amount of contrast medium which can be injected until the reference injection amount acquired from the reference injection amount storage unit 23 is reached, by subtracting the cumulative injection amount calculated by the contrast medium injection amount cumulative calculation unit 25 from the reference injection amount. The injection amount comparing unit 33 compares the cumulative injection amount calculated by the contrast medium injection amount cumulative calculation unit 25 with the reference injection amount acquired from the reference injection amount storage unit 23, thereby repeatedly calculating the ratio of the cumulative injection amount to the reference injection amount in %. Letting Va be the cumulative injection amount, and Vth be the reference injection amount, a ratio P(%) is calculated by $$P=(Va/Vth)\times100[\%]$$

The display control unit 27 is provided to generate an injection amount management information window including the ratio P of the cumulative injection amount to the reference injection amount, which is calculated by the injection amount comparing unit 33, and display it on the display 28. The injection amount management information window will be described in detail later. Briefly stated, in this window, a reference injection amount, cumulative injection amount, and possible injection amount are numerically displayed, and the ratio P of the cumulative injection amount to the reference injection amount is displayed numerically or in the form of a bar graph.

This display form of a bar graph changes stepwise in accordance with the ratio P of the cumulative injection amount to the reference injection amount.

Figure 4:
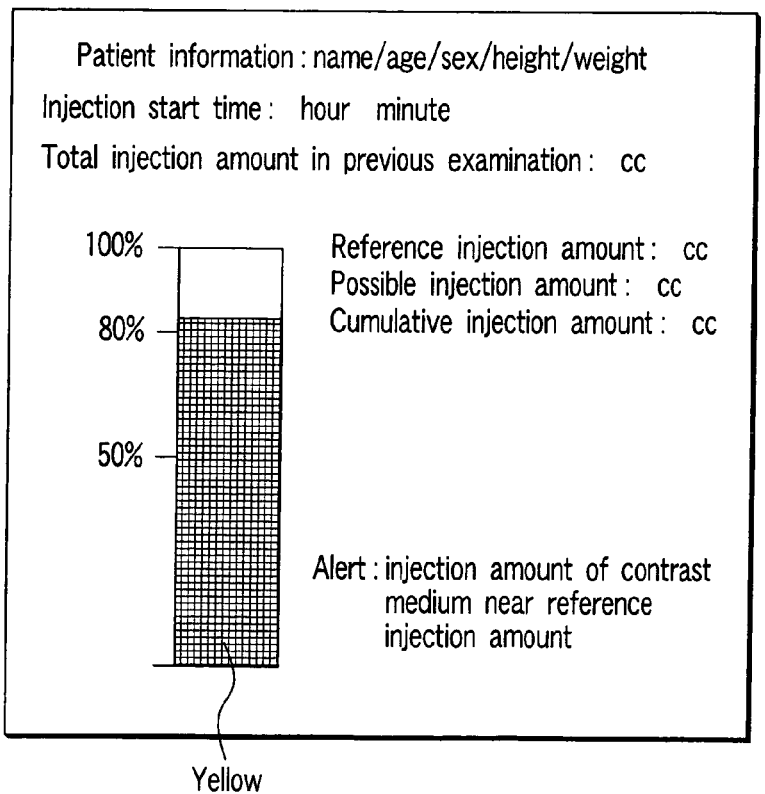
FIG. 4 is a view showing an example of a contrast medium injection amount management window when the cumulative injection amount exceeds 80% of the reference injection amount in this embodiment.

When, for example, the cumulative injection amount exceeds a predetermined ratio with respect to the reference injection amount, e.g., 80% of the reference injection amount, a bar graph may be displayed in yellow to attract a preliminary attention (see FIG. 4). In addition, when the ratio P exceeds 80%, an early alert message for attracting attention to the fact that the cumulative injection amount has exceeded 80% of the reference injection amount is displayed in the injection amount management information window (see FIG. 4).

Figure 3:
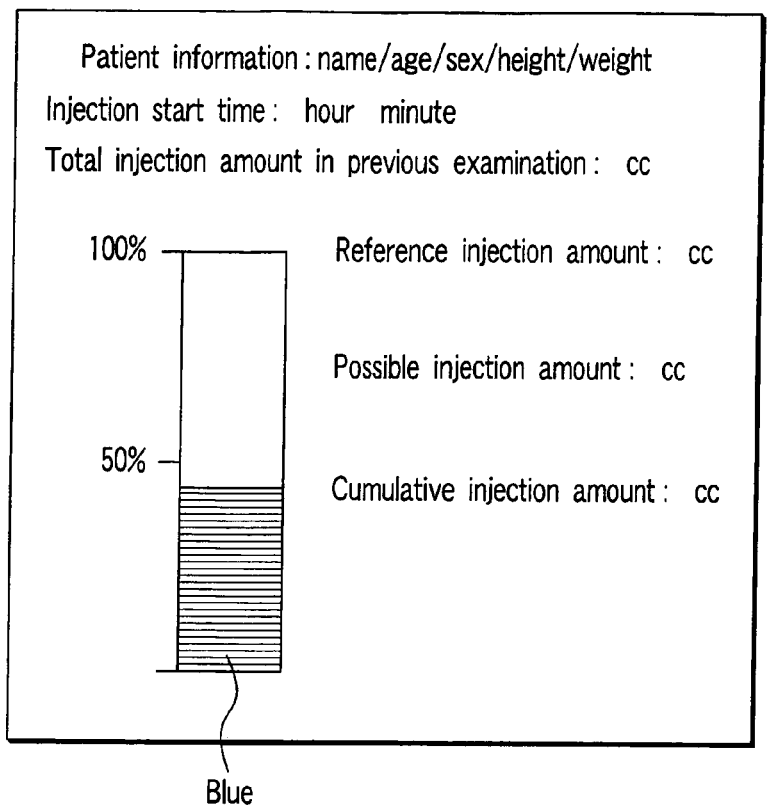
FIG. 3 is a view showing an example of a contrast medium injection amount management window in a normal state in this embodiment.

Note that when the cumulative injection amount is equal to or less than 80% of the reference injection amount, the bar graph is displayed in, for example, blue (see FIG. 3).

Figure 5:
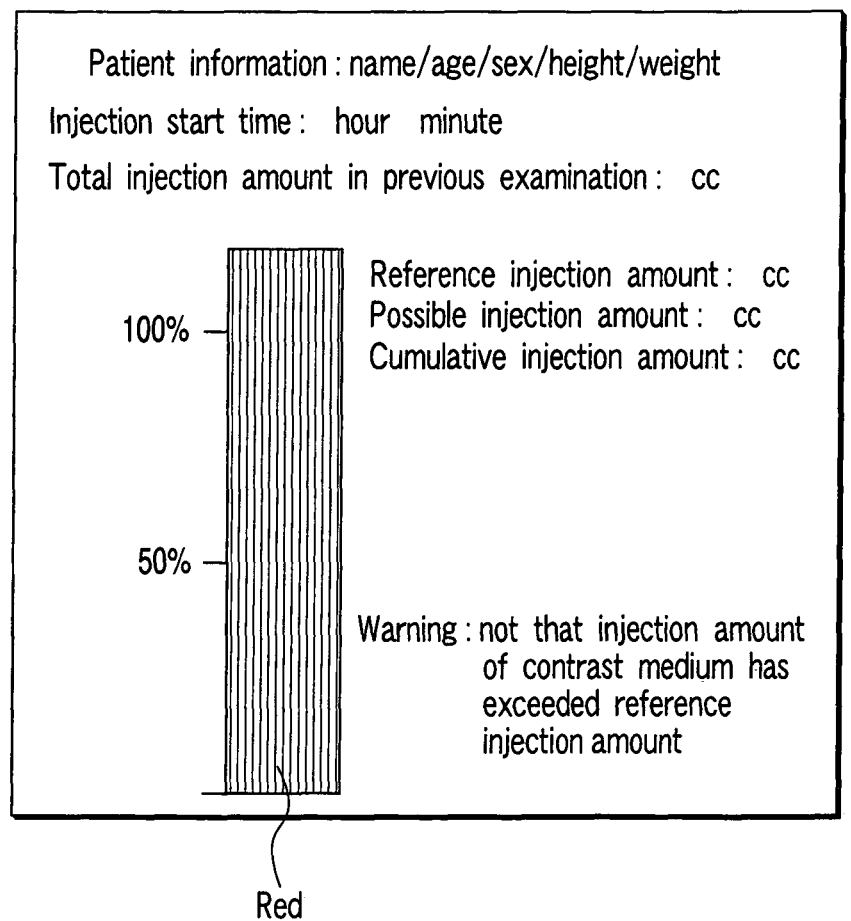
FIG. 5 is a view showing an example of a contrast medium injection amount management window when the cumulative injection amount exceeds the reference injection amount in this embodiment.

When the cumulative injection amount exceeds the reference injection amount, i.e., the ratio P exceeds 100%, the color of the bar graph changes to, for example, red to make a warning (see FIG. 5). In addition, when the ratio P exceeds 100%, the amount by which the cumulative injection amount exceeds the reference injection amount is numerically displayed. Furthermore, when the ratio P exceeds 100%, a warning message for making a warning that the cumulative injection amount has exceeded the reference injection amount is displayed in the injection amount management information window (see FIG. 5).

The ratio to the reference injection amount which is used to change the display form of this bar graph can be arbitrarily changed by the operator. The injection amount data storage unit 26 stores the data of the cumulative injection amount at the end of the examination, together with the subject information and examination information.

Contrast medium injection amount managing operation in this embodiment will be described next.

Before the start of actual examination, the data of the examination routine planed by the examination planning unit 13 is supplied from the examination information memory 8 to an injection planning unit 39. The examination routine data contains a sequence of a plurality of imaging steps and the injection amount of contrast medium used in each imaging step. The injection planning unit 39 calculates the total injection amount of contrast medium used in a plurality of imaging steps contained in the examination routine as an estimated cumulative injection amount Ve of contrast medium used in the examination routine. The injection planning unit 39 compares the estimated cumulative injection amount Ve with the reference injection amount provided from the reference injection amount storage unit 23. If the estimated cumulative injection amount Ve exceeds the reference injection amount, the injection planning unit 39 causes the image display unit 12 to display a message for warning that the estimated cumulative injection amount Ve exceeds the reference injection amount. In addition to the warning message, the flow of an examination routine and the amount of contrast medium used in each imaging step are displayed. By operating the operation unit 34, the amount of contrast medium (injection speed or time) used in each imaging step is arbitrarily changed such that the estimated cumulative injection amount Ve does not exceed the reference injection amount. After the start of the examination, the injection planning unit 39 calculates the value or absolute value of the difference (Va–Va') between a cumulative injection amount Va calculated by the contrast medium injection amount cumulative calculation unit 25 at the current point of time and an estimated cumulative injection amount Va' at the current point of time which is estimated from the estimated injection amount in each imaging step in the examination routine. The estimated cumulative injection amount Va' at the current point of time and the difference (Va–Va') are numerically displayed on the display 28. The larger the difference (Va–Va'), the larger the injection amount of contrast medium than the planned amount, i.e., the higher the injection speed. When the difference (Va–Va') exceeds a predetermined value, a message indicating that the actual injection amount of contrast medium is larger than the planned amount is displayed on the display 28. At the same time, the display form of the estimated cumulative injection amount Va' at the current point of time and the difference (Va–Va') changes in color to, for example, red, or changes to blinking display. The predetermined value to be compared with the difference (Va–

Va') is set to, for example, an arbitrary ratio to the reference injection amount Vth, e.g., 10%. This ratio can be arbitrarily set and modified on the user or maker side. The injection planning unit 39 modifies the estimated cumulative injection amount Ve at the end of the examination with (Ve+(Va−Va')) from the difference (Va−Va') between the actual injection amount of contrast medium and the planned amount. The modified estimated cumulative injection amount Ve is numerically displayed on the display 28. When the modified estimated cumulative injection amount Ve exceeds the reference injection amount Vth, the display form of the estimated cumulative injection amount Ve changes in color to, for example, red, or changes to blinking display.

Figure 2:
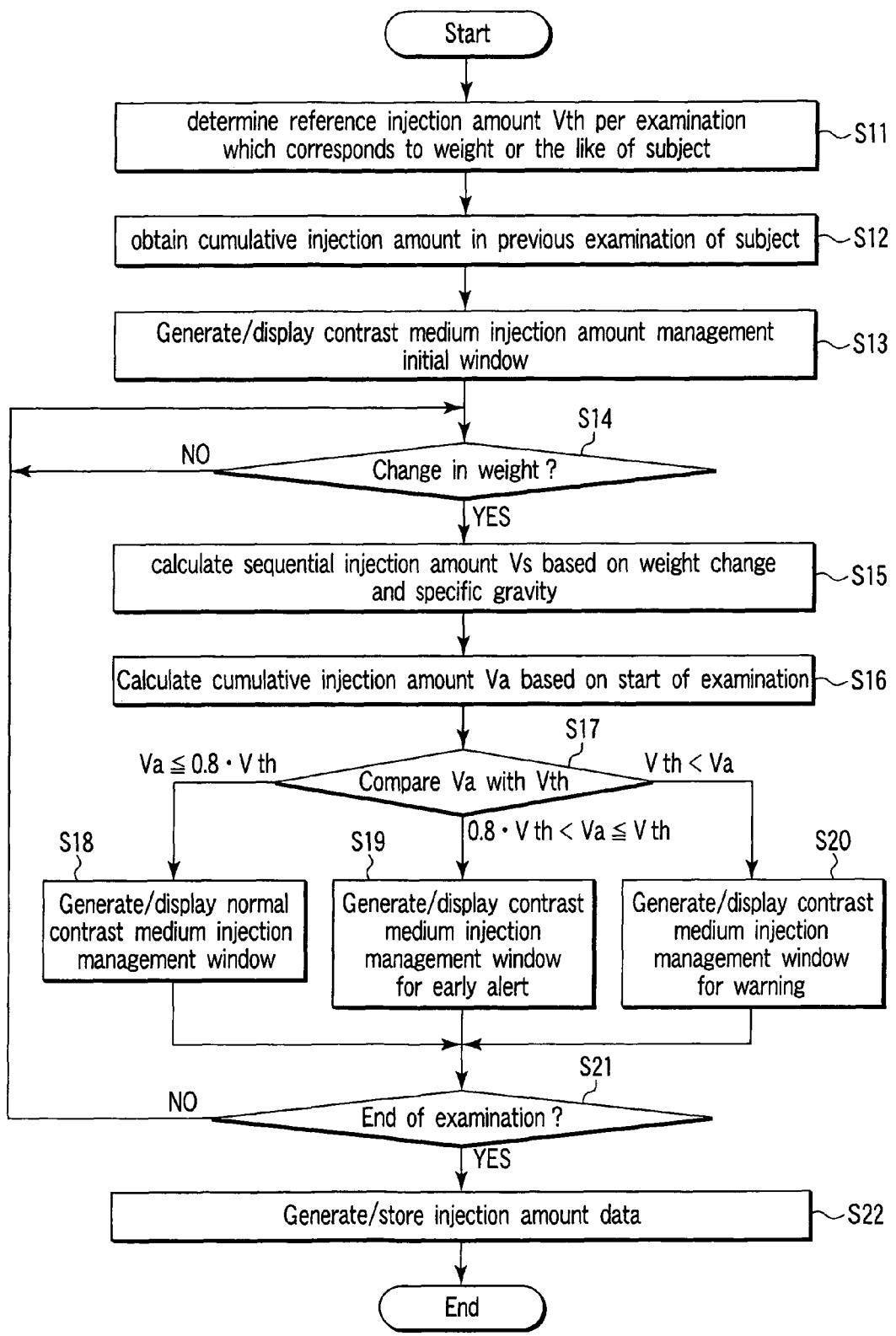
FIG. 2 is a flowchart showing a sequence of contrast medium injection amount managing operation in this embodiment.

FIG. 2 shows a sequence of contrast medium injection amount managing operation in this embodiment. For the sake of descriptive convenience, assume that a contrast medium is injected from only the injection apparatus 36 of the contrast medium bottle 37 into the subject. Before the start of examination, the contrast medium injection management control unit 21 acquires the data of a reference injection amount corresponding to the patient weight of examination information from the reference injection amount storage unit 23 (S11). The data of the reference injection amount is supplied to the injection amount comparing unit 33 and the display control unit 27. The contrast medium injection management control unit 21 acquires the data of a cumulative injection amount in the previous examination associated with the subject to be examined this time from the injection amount data storage unit 26 (S12). The data of the cumulative injection amount in the previous examination is supplied to the display control unit 27. In addition, the data of the name, age, sex, height, and weight of the patient information in the examination information are supplied from the examination information memory 8 to the display control unit 27. Furthermore, the data of a cumulative injection amount from the cumulative calculation unit 25 and the data of the ratio P of the cumulative injection amount to the reference injection amount from the injection amount comparing unit 33 are supplied to the display control unit 27 under the control of the contrast medium injection management control unit 21.

The display control unit 27 generates contrast medium injection amount management window data shown in FIG. 3 from the supplied data, and causes the display 28 provided exclusively for the display of contrast medium information to display the window (S13). The contrast medium injection amount management window includes name, age, sex, height, weight, the start time of contrast medium injection, the total injection amount in the previous examination, the reference injection amount, and the cumulative injection amount as character/numeral information. The contrast medium injection amount management window also includes the bar graph generated by the display control unit 27 on the basis of the ratio P of the cumulative injection amount to the reference injection amount. The area portion corresponding to the ratio P in the rectangular figure corresponding to the reference injection amount is indicated in a different color as a display form. Before the start of the injection of a contrast medium, since the ratio P is zero, there is no portion to be indicated in a different color.

After the start of the injection of a contrast medium, the weight sensor control unit 31 starts measuring the weight of the contrast medium bottle 37 through the weight sensor 32. Weight measurement is repeated in predetermined cycles, and the weight data of the contrast medium bottle 37 is repeatedly output from the weight sensor control unit 31. The weigh data from the contrast medium bottle 37 is supplied from the weight sensor control unit 31 to the contrast medium injection amount sequential calculation unit 24. The contrast medium injection amount sequential calculation unit 24 calculates the difference between the previously measured weight and the currently measured weight. If the difference is not zero (S14), the contrast medium injection amount sequential calculation unit 24 determines that a weight change has occurred, i.e., a contrast medium has been injected in the interval between the previous measurement time and the current measurement time, and calculates an injection amount (volume) Vs from the weight change and a specific gravity corresponding to the information of the contrast medium used selectively acquired from the contrast medium specific gravity data storage unit 22 according to the contrast medium type information of the examination information (S15). The cumulative calculation unit 25 calculates the cumulative injection amount Va by accumulating injection amounts Vs from the start of the examination (S16).

Note that when the contrast medium bottle 37 is replaced, the weight abruptly changes as the bottle 37 is detached. This typically occurs as a change of a predetermined amount within a predetermined period of time, e.g., an abrupt change of 50 cc or more occurs within 10 sec or less. The calculation unit 24 or 25 detects this abrupt change, and determines that the bottle 37 has been replaced and does not regard this as the injection amount of contrast medium. The sequential calculation unit 24 resets a weight value when the weight increases next, and monitors a decrease in weight again. Obviously, the cumulative calculation unit 25 continuously uses the cumulative injection amount without resetting it even if the bottle 37 is replaced.

The injection amount comparing unit 33 compares the cumulative injection amount Va with the reference injection amount Vth (S17). In practice, the injection amount comparing unit 33 calculates the ratio P of the cumulative injection amount Va to the reference injection amount Vth. The injection amount comparing unit 33 calculates the possible injection amount of contrast medium that can be injected until the reference injection amount Vth is reached by subtracting the cumulative injection amount Va from the reference injection amount Vth. The data of the comparison result (ratio P) of the cumulative injection amount Va with respect to the reference injection amount Vth is supplied to the display control unit 27, together with the data of the possible injection amount and cumulative injection amount Va. The display control unit 27 generates a window corresponding to the comparison result of the cumulative injection amount Va with respect to the reference injection amount Vth (S18, S19, and S20).

As the display forms of an injection amount management information window, three patterns are prepared in accordance with increases in cumulative injection amount:
1) when the cumulative injection amount Va is equal to or less than 80% of the reference injection amount Vth ($P \leq 0.8$);
2) when the cumulative injection amount Va exceeds 80% of the reference injection amount Vth, and the cumulative injection amount Va is equal to or less than the reference injection amount Vth ($0.8 < P \leq 1$); and
3) when the cumulative injection amount Va exceeds the reference injection amount Vth ($1 < P$).

Pattern 1) corresponds to a normal window (S18). Pattern 2) corresponds to an early alert window (S19). Pattern 3) corresponds to a warning window (S20).

FIG. 3 shows an example of a normal window corresponding to pattern 1) described above. As described above, the contrast medium injection amount management window includes name, age, sex, height, weight, the start time of contrast medium injection, the total injection amount in the previous examination, the reference injection amount, and the cumulative injection amount as character/numeral information. In addition, the ratio P of the cumulative injection amount to the reference injection amount is displayed in the form of a bar graph. Since the area portion corresponding to the ratio P in the entire region of the bar graph is indicated in a different color, the current state of the injection amount can be easily comprehended visually. More specifically, the bar graph is displayed in "white" as a basic color, and the area portion corresponding to the ratio P is displayed in "blue" on the graph.

FIG. 4 shows an early alert window corresponding to pattern 2) described above. When the ratio P of the cumulative injection amount Va to the reference injection amount Vth exceeds 80% of the reference injection amount, the color of the area portion on the bar graph changes from "blue" to "yellow". When the ratio P exceeds 80%, in the injection amount management information window, an early alert message for calling attention to the fact that the cumulative injection amount has exceeded 80% of the reference injection amount is displayed. This calls operator's attention to the fact that the injection amount of contrast medium has approached near the reference injection amount.

FIG. 5 shows a window corresponding to pattern 3) described above. When the cumulative injection amount Va exceeds the reference injection amount Vth, the area portion corresponding to the cumulative injection amount Va is enlarged with respect to a portion corresponding to the reference injection amount Vth in accordance with the ratio P in the bar graph. The color of the area portion in the bar graph changes from "yellow" to "red", and the red area portion blinks. The excessive injection amount calculated by the injection amount comparing unit 33 is numerically displayed. The excessive injection amount is the amount by which the cumulative injection amount Va exceeds the reference injection amount Vth. In addition, when the cumulative injection amount exceeds the reference injection amount, a warning message for warning that the cumulative injection amount has exceeded the reference injection amount is displayed. The above change in display form makes it possible to strongly call operator's attention to the fact that the injection amount of contrast medium has exceeded the reference injection amount.

In this embodiment, even if the cumulative injection amount reaches the reference injection amount, no action is taken to urgently stop the injection of the contrast medium or no message for prompting urgent stop of injection is displayed. The embodiment does not go beyond strongly calling attention to the fact that the injection amount of contrast medium has exceeded the reference injection amount. This is because the reference injection amount is set to a value smaller than the limit value for living bodies (upper limit value for safety). This can prevent as much as possible the injection of a contrast medium from being interrupted as the injection amount of contrast medium reaches its limit before the completion of necessary contrast examination.

A series of operations from S14 to S20 described above is repeated in predetermined very short cycles, e.g., 0.1 sec, until the end of the examination (S21). An imaging operator can quickly comprehend the injection amount of contrast medium and the current injection ratio and can execute examination while considering a contrast medium injection plan to the end of the examination to some extent.

After the end of the examination, the final cumulative injection amount is determined as the total injection amount for the current examination, and is stored in the injection amount data storage unit 26, together with the subject information and the examination information (S20).

As has been described above, according to this embodiment, the management accuracy of the injection amount of contrast medium can be improved, and a contrast medium can be injected according to a plan. This makes it possible to reduce the unnecessary injection amount of contrast medium and prevent the interruption of examination due to excessive injection of the contrast medium.

The examination is required for the above-mentioned embodiment to be done by the predetermined examinating routine. However, The cumulative injection amount Va' is not estimated in the intervention to which the routine has not been predetermined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A contrast medium injection management apparatus for use with an image diagnostic apparatus, comprising:
    a measuring unit which repeatedly measures the injection amount of contrast medium injected from at least one contrast medium injection device into a subject to be examined;
    a cumulative injection amount calculating unit which repeatedly calculates a cumulative injection amount at the start of examination or after an arbitrary point of time from the injection amount; and
    a display unit which displays the cumulative injection amount, and a warning message representing that the cumulative injection amount exceeds a reference injection amount, the display unit being shared with an image displaying unit of the image diagnostic apparatus.

2. An apparatus according to claim 1, wherein the measuring unit measures a total injection amount of contrast medium injected from said at least one contrast medium injection device into the subject.

3. An apparatus according to claim 1, wherein the measuring unit has a weight sensor which measures a weight of a contrast medium bottle.

4. An apparatus according to claim 3, wherein the measuring unit has a volume calculating unit which calculates the injection amount of contrast medium as a volume on the basis of a change in the weight of the contrast medium bottle and a specific gravity of the contrast medium.

5. An apparatus according to claim 1, wherein the measuring unit has a sensor which measures an amount of contrast medium passing through a catheter or a tube connected to the catheter.

6. An apparatus according to claim 1, further comprising a ratio calculating unit which calculates a ratio of the cumulative injection amount to the reference injection amount.

7. An apparatus according to claim 6, wherein the display unit displays a ratio of the cumulative injection amount to the reference injection amount in the form of a bar graph.

8. An apparatus according to claim 7, wherein the display unit changes a display form of the bar graph stepwise in accordance with the ratio of the cumulative injection amount to the reference injection amount.

9. An apparatus according to claim 6, wherein the display unit numerically displays the ratio of the cumulative injection amount to the reference injection amount.

10. An apparatus according to claim 7, wherein the display unit makes the display form of the bar graph obtained when the cumulative injection amount exceeds the reference injection amount differ from the display form of the bar graph obtained when the cumulative injection amount does not exceed the reference injection amount.

11. An apparatus according to claim 1, wherein the display unit numerically displays an excessive amount by which the cumulative injection amount exceeds the reference injection amount.

12. An apparatus according to claim 7, wherein the display unit makes the display form of the bar graph obtained when the cumulative injection amount exceeds a predetermined ratio to the reference injection amount differ from the display form of the bar graph obtained when the cumulative injection amount does not exceed the predetermined ratio to the reference injection amount.

13. An apparatus according to claim 1, wherein the display unit displays an early alert message when the cumulative injection amount has exceeded a predetermined ratio to the reference injection amount.

14. An apparatus according to claim 1, wherein the display unit displays a warning message when the cumulative injection amount has exceeded the reference injection amount.

15. An apparatus according to claim 1, further comprising a storage unit which stores data of the cumulative injection amount together with information of the subject and examination information.

16. An image diagnostic apparatus comprising a contrast medium injection management apparatus defined in claim 1.

17. A contrast medium injection apparatus comprising a contrast medium injection management apparatus defined in claim 1.

18. A contrast medium injection management apparatus for use with an image diagnostic apparatus comprising:

a measuring unit which repeatedly measures the injection amount of contrast medium injected from at least one contrast medium injection device into a subject to be examined;

a cumulative injection amount calculating unit which repeatedly calculates a cumulative injection amount at the start of examination or after an arbitrary point of time from the injection amount;

a display unit which displays an early alert message when the cumulative injection amount exceeds a predetermined ratio to a reference injection amount, the display unit being shared with an image displaying unit of the image diagnostic apparatus, and displays a warning message when the cumulative injection amount exceeds the reference injection amount.

19. A contrast medium injection management apparatus for use with an image diagnostic apparatus comprising:

a measuring unit which repeatedly measures the injection amount of contrast medium injected from at least one contrast medium injection device into a subject to be examined;

a cumulative injection amount calculating unit which repeatedly calculates a cumulative injection amount at the start of examination or after an arbitrary point of time from the injection amount; and a display unit which displays an early alert message when the cumulative injection amount exceeds a predetermined ratio to a reference injection amount, the display unit being shared with an image displaying unit of the image diagnostic apparatus.

\* \* \* \* \*